(12) United States Patent
Nakanishi

(10) Patent No.: US 6,561,801 B1
(45) Date of Patent: May 13, 2003

(54) LIGHT GUIDE UNIT, METHOD FOR PRODUCING THE SAME, AND DENTAL HANDPIECE HAVING LIGHT GUIDE UNIT

(75) Inventor: Takasuke Nakanishi, Kanuma (JP)

(73) Assignee: Nakanishi Inc., Tochigi-ken (JP)

( * ) Notice: Subject to any disclaimer, the term of this patent is extended or adjusted under 35 U.S.C. 154(b) by 0 days.

(21) Appl. No.: 09/561,650

(22) Filed: May 2, 2000

(30) Foreign Application Priority Data

May 12, 1999 (JP) .......................... 11-130844

(51) Int. Cl.⁷ .............................. A61C 1/00; A61C 3/00
(52) U.S. Cl. .......................... 433/29; 385/117
(58) Field of Search .................. 433/29; 385/117, 385/115, 106, 112; 264/1.28

(56) References Cited

U.S. PATENT DOCUMENTS

| | | | |
|---|---|---|---|
| 4,076,377 A | * | 2/1978 | Moraschetti ............ 350/96.25 |
| 4,143,942 A | * | 3/1979 | Anderson ................ 350/96.23 |
| 4,173,392 A | | 11/1979 | Ekinaka et al. |
| 4,518,355 A | * | 5/1985 | Hoffmeister et al. ......... 433/29 |
| 4,923,268 A | * | 5/1990 | Xu .......................... 350/96.15 |
| 4,983,121 A | | 1/1991 | Straihammer et al. |
| 5,386,489 A | | 1/1995 | Stokes |
| 5,683,246 A | | 11/1997 | Coss et al. |

FOREIGN PATENT DOCUMENTS

| | | |
|---|---|---|
| DE | 39 10474 A1 | 4/1990 |
| DE | 29712789 U1 | 11/1997 |
| EP | 0903593 A1 | 3/1999 |
| JP | 63-143311 | 9/1988 |
| JP | 07-275261 | 10/1995 |

OTHER PUBLICATIONS

European Search Report for Application No. 00303591.2–2318, dated May 29, 2002.

* cited by examiner

*Primary Examiner*—Nicholas D. Lucchesi
(74) *Attorney, Agent, or Firm*—Reed Smith Crosby Heafey LLP

(57) ABSTRACT

There is disclosed a light guide unit including a bunch of glass fibers capable of transmitting light from a light source to a desired site, a sheath of a thermocontracting resin contracted to cover the bunch of glass fibers for substantially its overall length, and a filler of a hardening resin hardened to fill spaces between the glass fibers within the sheath. Also disclosed are a method for producing the light guide unit, and a dental handpiece having the light guide unit.

9 Claims, 3 Drawing Sheets

(a)

(b)

LIGHT GUIDE UNIT, METHOD FOR PRODUCING THE SAME, AND DENTAL HANDPIECE HAVING LIGHT GUIDE UNIT

FIELD OF THE INVENTION

The present invention relates to a light guide unit suitable for installation in an instrument, such as a dental handpiece, for transmitting light from a light source to a desired site, a method for producing the light guide unit, and a dental handpiece having the light guide unit installed therein.

BACKGROUND OF THE INVENTION

A variety of medical or industrial instruments have a lighting system for illuminating a desired site, including a light source and a light guide unit installed in an instrument for transmitting light from the light source to a desired site.

For example, in a conventional dental handpiece with a coupler, a light source such as a halogen lamp is placed in the coupler, and a light guide unit is accommodated in a channel provided through the handpiece for transmitting light from the light source to the head or neck portion of the handpiece. The light thus transmitted through the light guide unit is projected through one or more windows provided in the head or neck portion to illuminate the treatment site.

The channel extends generally axially through the handpiece, and is curved gently with varying cross-sectional shapes. The light guide unit accommodated in the channel is thus required to be deformed to conform to the interior shape of such channel.

An example of such a conventional light guide unit is shown in FIGS. 3(a) and 3(b), designated as light guide unit 30. The light guide unit 30 is composed of a plurality of glass fibers 33, which are bunched together at their ends with metal tubes 31, 32. The bunch of glass fibers may be branched at one end as shown, if desired, and the end of each branch is bunched similarly with a metal tube 31. The metal tubes 31, 32 at the ends of the bunch or the branches are filled with an adhesive to fix the fibers together.

The light guide unit 30 has middle section 35 wherein the glass fibers 33 are not bound together with an adhesive or a metal tube, but are independent from each other. This section 35, on one hand, enables free deformation of the light guide unit 30 to conform to the interior shape of the channel, but on the other hand, the free glass fibers in this section 35 are easily broken and damaged, which causes problems in handling.

SUMMARY OF THE INVENTION

It is therefore an object of the present invention to provide a light guide unit that is hard to be broken in handling and that conforms to the interior shape of the channel in which the unit is to be seated.

It is another object of the present invention to provide a method for producing a light guide unit that facilitates production of a light guide unit having sufficient mechanical strength, and that enables easy production of a light guide unit with any configuration in conformity with the interior shape of the channel in which the unit is to be seated.

It is a yet another object of the present invention to provide a dental handpiece having a light guide unit that is hard to be broken in handling.

According to the present invention, there is provided a light guide unit comprising:

a bunch of glass fibers capable of transmitting light from a light source to a desired site, a sheath of a thermocontracting resin contracted to cover said bunch of glass fibers for substantially its overall length, and a filler of a hardening resin hardened to fill spaces between said glass fibers within said sheath.

According to the present invention, there is also provided a method for producing a light guide unit comprising a bunch of glass fibers capable of transmitting light from a light source to a desired site, a sheath of a thermocontracting resin contracted to cover said bunch of glass fibers for substantially its overall length, and a filler of a hardening resin hardened to fill spaces between said glass fibers within said sheath, said method comprising:

placing a bunch of glass fibers capable of transmitting light in a sheath of a thermocontracting resin, filling an interior of said sheath with a filler of a hardening resin so that spaces between said glass fibers are filled with said filler, thereby preparing a sheathed product, molding a sheathed product in a mold having a desired cavity configuration by applying heat and pressure, and hardening said filler to fix a configuration of a light guide unit.

According to the present invention, there is further provided a dental handpiece comprising:

a light guide unit for transmitting light from a light source to a treatment site, a channel for accommodating said light guide unit therein, and a light projection window in alignment with one end of said light guide unit for projecting light transmitted through the light guide unit onto a treatment site, wherein said light guide unit further comprises, a bunch of glass fibers capable of transmitting light from a light source to a treatment site, a sheath of a thermocontracting resin contracted to cover said bunch of glass fibers for substantially its overall length, and a filler of a hardening resin hardened to fill spaces between said fiber optics within said sheath.

DETAILED DESCRIPTION OF THE PREFERRED EMBODIMENTS

The present invention will now be explained in detail with reference to a preferred embodiment taken in conjunction with the attached drawings, but the present invention is not limited to the embodiment.

Figure 1:
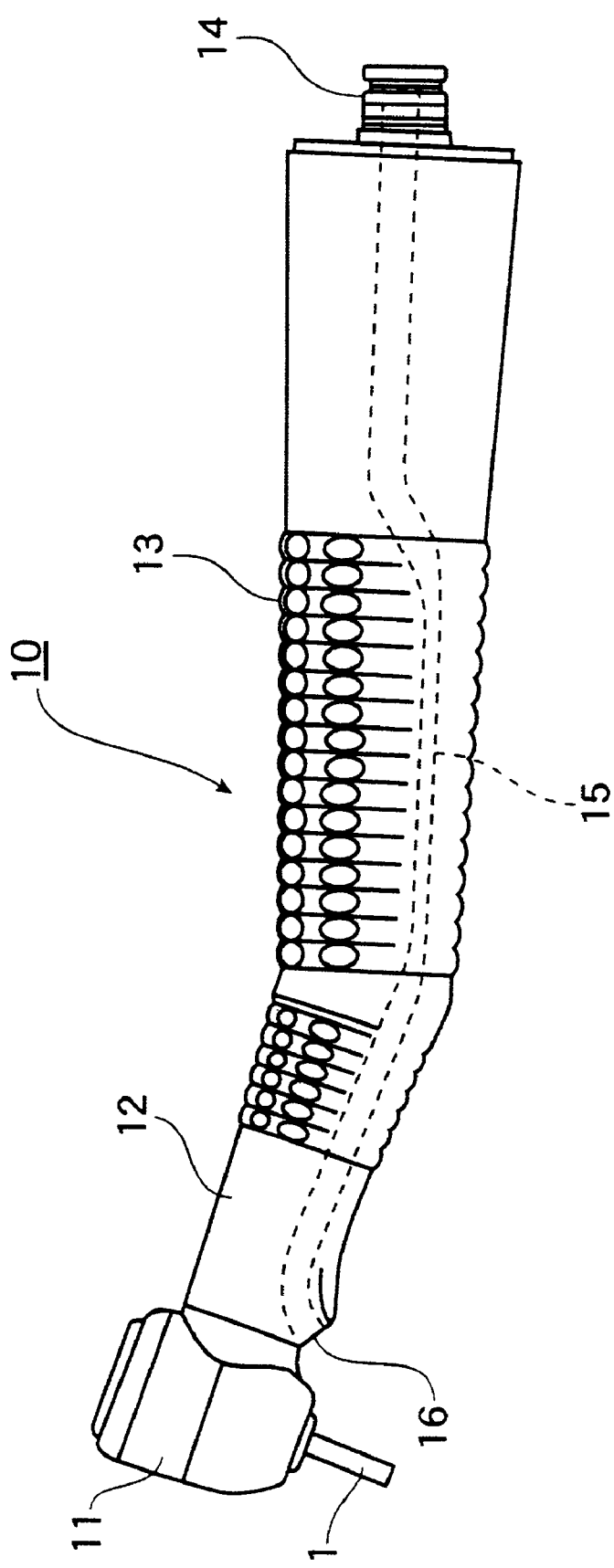
FIG. 1 is a side view of an embodiment of a dental handpiece of the present invention.

FIG. 1 shows a side view of an embodiment of a dental handpiece 10 of the present invention. The handpiece 10 includes a head 11 for detachably holding a dental treatment tool 1, a neck portion 12 extending proximally from the head 11, a grip portion 13 extending at an angle from the neck portion 12 and to be grasped by an operator, and a connecting portion 14 provided at the proximal end of the grip portion 13 for connection with a coupler (not shown). The coupler accommodates a light source (not shown), and connects the handpiece 10 to a dental unit (not shown) or dental hose (not shown) in a conventional manner.

The handpiece 10 is provided with a through channel 15 extending generally axially from the connecting portion 14 and terminating at one or more windows 16 provided in the neck portion 12. In this channel 15 is seated a light guide unit 20 (FIG. 2), with the distal end of the unit 20 being in alignment with the windows 16. The unit 20 transmits light from the light source in the coupler to the windows 16 for projection therethrough.

A light guide unit of the present invention, such as the light guide unit 20, has a bunch of glass fibers capable of transmitting light from a light source to a desired site, a sheath of a thermocontracting resin contracted to cover the bunch of glass fibers for substantially its overall length, and a filler of a hardening resin hardened to fill the spaces between the glass fibers within the sheath.

The size of the light guide unit is not particularly limited, and may be designed depending on the size of the instrument, such as a handpiece, in which the unit is to be installed. The cross-section of the light guide unit maybe designed in different shapes and sizes from portion to portion, to conform to the space in which the light guide unit is to be seated.

The diameter of each glass fiber is not particularly limited, but is usually 20 to 50 µm.

The thermocontracting resin constituting the sheath may be any resin as long as it contacts upon heating at a predetermined temperature. For example, polyethylene fluoride such as Teflon (trademark), urethane, silicone, and vinyl chloride resins may be used. The sheath covers the bunch of glass fibers for substantially its overall length for binding the fibers together to reinforce the mechanical strength of the unit.

The hardening resin constituting the filler may be a thermosetting resin that hardens upon heating at a predetermined temperature, an anaerobic resin that hardens with the lapse of time, or an ultraviolet curable resin that hardens upon irradiation with ultraviolet rays. Examples of a thermosetting resin include epoxy resins and phenol resins. The filler fills the spaces between the glass fibers within the sheath to fix the fibers together for further reinforcing the mechanical strength of the unit.

Figure 2:
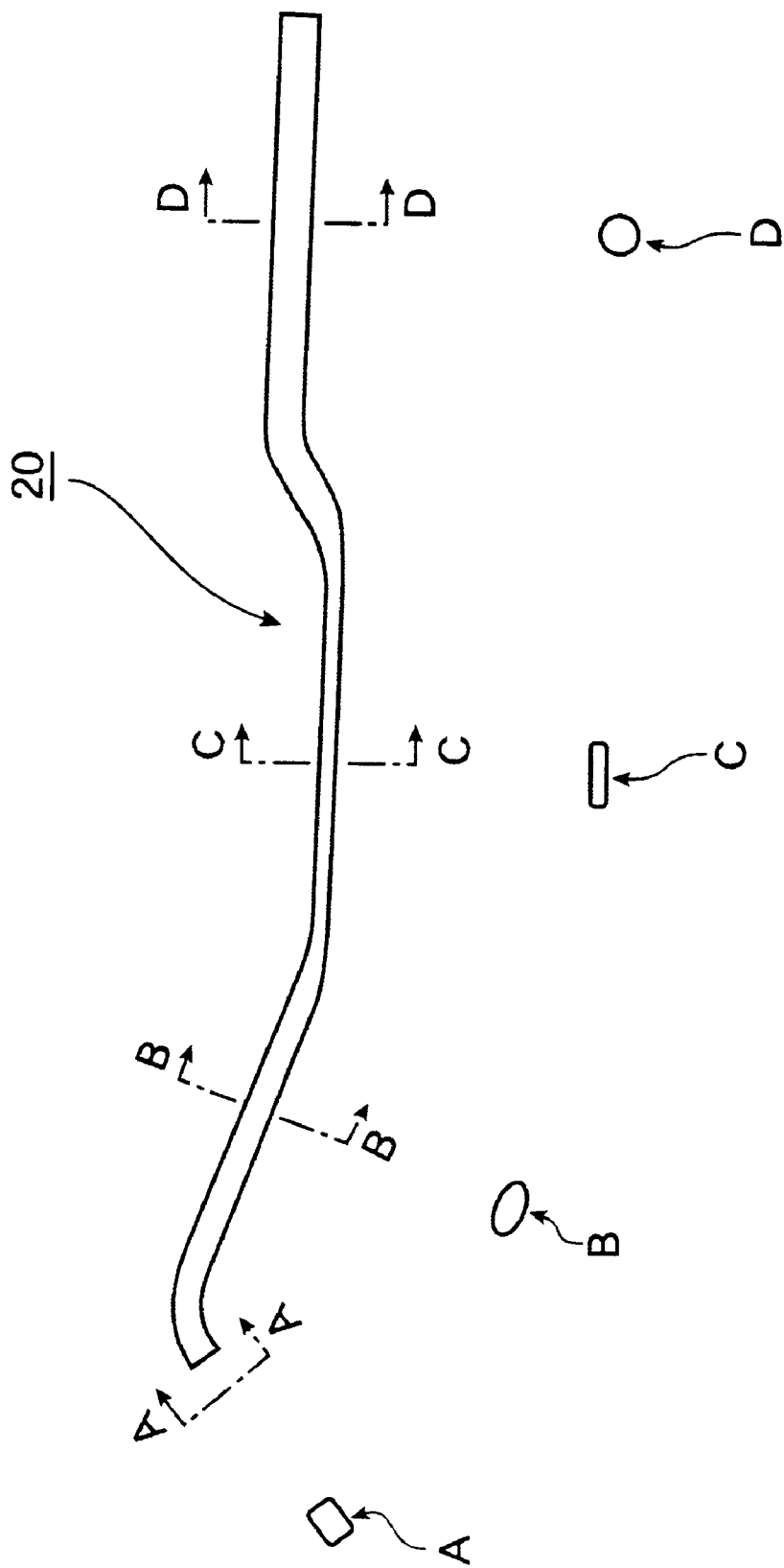
FIG. 2 is a side view of an embodiment of a light guide unit according to the present invention to be seated in the handpiece of FIG. 1, with illustrations of respective cross-sections taken along lines A—A, B—B, C—C, and D—D in the side view.
Figure 3:
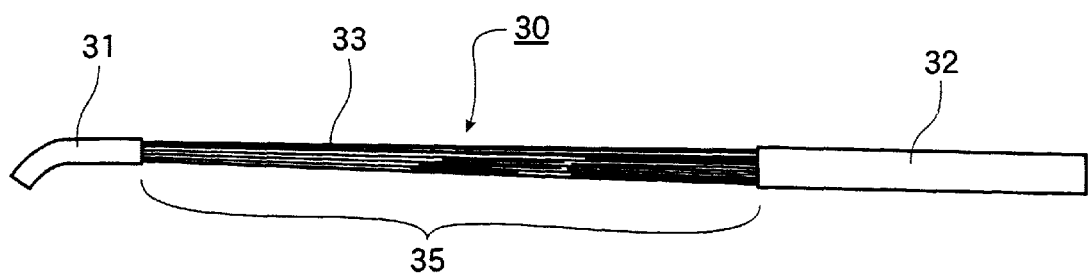
FIG. 3(a) is a side view of a conventional light guide unit.
FIG. 3(b) is a plan view thereof.
Figure 3:
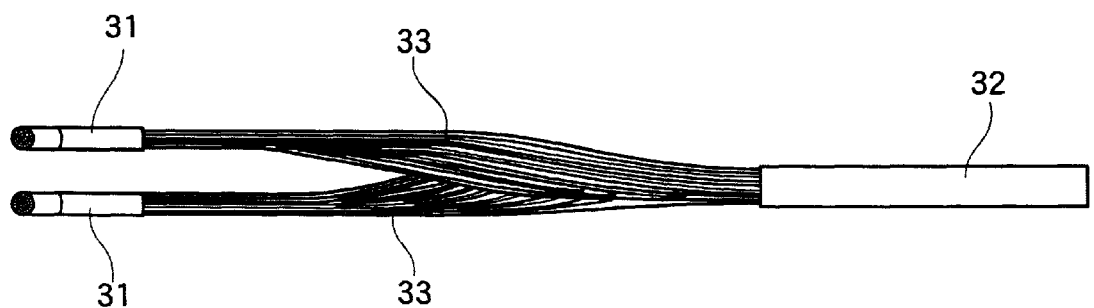

FIG. 2 shows an example of the general contour and cross-sections of a light guide unit 20 of the present invention. The light guide unit 20 is curved gently as seen in the side view, and has varying cross-sectional shapes as seen in the cross-sectional views. Specifically, the cross-section A taken along line A—A is rectangular, the cross-section B taken along line B—B is elliptic, the cross-section C taken along line C—C is flat rectangular, and the cross-section D taken along line D—D is circular.

The light guide unit of the present invention may be installed in a dental handpiece such as the one shown in FIG. 1, for transmitting light from a light source to a treatment site. However, the unit maybe installed in other instruments as well, such as other medical instruments including surgical handpieces, or other industrial instruments, for transmitting light from a light source to a desired site.

The light guide unit of the present invention may be produced by the method of the present invention as follows.

A bunch of glass fibers capable of transmitting light is placed in a sheath of a thermocontracting resin. The diameter of each glass fiber is not particularly limited, but is usually 20 to 50 µm as mentioned above with respect to the light guide unit. The diameter of the bunch is not particularly limited, either, and may be decided depending on the size of the space in which the resulting light guide unit is to be seated. When the light guide unit is to be seated in an average dental handpiece, the diameter of the bunch is usually 1 to 4 mm.

The diameter of the sheath of a thermocontracting resin is not particularly limited as long as the sheath can accommodate the bunch of glass fibers therein. For the convenience in manufacture, the sheath may preferably have an inner diameter that is slightly larger than the diameter of the bunch. The length of the sheath is preferably determined taking the contraction upon heating into account, so that the sheath covers substantially the overall length of the bunch after the heat contraction.

The thermocontracting resin constituting the sheath may be selected from those listed above with respect to the light guide unit.

Next, the interior of the sheath is filled with a filler of a hardening resin so that the spaces between the glass fibers are filled with the filler, to thereby prepare a sheathed product. The hardening resin constituting the filler may be selected from those listed above with respect to the light guide unit.

The sheathed product is then molded in a mold having a desired cavity configuration by applying heat and pressure.

The mold may preferably be a two-piece metal mold that can be split into halves for operational convenience. The cavity of the mold forms the configuration of the light guide unit to be produced. In other words, the cavity has the configuration that conforms to the configuration of the space such as a channel in an instrument, e.g. a dental handpiece, in which the light guide unit is to be seated. When the channel is curved and has varying cross-sections, the cavity has the configuration corresponding to such curves and cross-sections, so that the light guide unit to be produced will have the configuration that is complementary to the channel in which it is to be seated.

When the sheathed product is molded in a mold by applying heat and pressure, the sheath of a thermocontracting resin contracts by the heat, the filler of a hardening resin spreads all over the spaces between the glass fibers within the sheath, and the sheathed product conforms to the cavity configuration.

The mold is preferably heated to a predetermined temperature before the sheathed product is placed in its cavity, but the heat and pressure may be simultaneously applied to the sheathed product in a mold.

The filler may be hardened while the sheathed product is molded, or after the sheathed product is molded. When the filler is a thermosetting resin, it is preferred to heat the sheathed product while the product is subjected to pressure, so that both the contraction of the sheath and the hardening of the filler proceed together. When the filler is an anaerobic resin, the molded product taken out of the mold may be left stand for hardening. When the filler is an ultraviolet curable resin, the molded product taken out of the mold may be irradiated with ultraviolet ray.

As discussed above, the light guide unit of the present invention includes a bunch of glass fibers that is covered with a sheath of a thermocontracting resin for substantially its overall length, and the spaces between the glass fibers are filled with a hardened hardening resin.

Thus, the light guide unit of the present invention has sufficient mechanical strength since the glass fibers are fixed in a predetermined shape by the sheath and the filler, and may be handled with less care for damage, compared to the extremely fragile conventional light guide unit wherein the glass fibers are not bound together for its overall length.

According to the method for producing a light guide unit of the present invention, a bunch of glass fibers are placed in a sheath of a thermocontracting resin, the interior of the sheath is filled with a filler of a hardening resin so that the spaces between the glass fibers are filled with the filler, and the resulting sheathed product is molded in a mold by applying heat and pressure. Thus, the sheath of a thermocontracting resin is contracted by heat into a desired shape corresponding to the cavity shape of the mold, and by the simultaneous or following hardening step, the filler is hardened to fix the configuration of the light guide unit. Accordingly, a light guide unit having sufficient mechanical strength and yet conforming to the configuration of the space in which the unit is to be seated, may be produced conveniently.

Since the dental handpiece of the present invention includes the light guide unit mentioned above, the handpiece may be handled with less care for damage, compared to the conventional dental handpiece having non-bound glass fibers.

Although the present invention has been described with reference to the preferred embodiments, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A light guide unit comprising:
   a bunch of glass fibers capable of transmitting light from a light source to a desired site,
   a sheath of a thermocontracting resin contracted to cover said bunch of glass fibers for substantially its overall length, and
   a filler of a hardening resin hardened to fill spaces between said glass fibers within said sheath.

2. The light guide unit of claim 1 wherein said hardening resin is selected from the group consisting of a thermosetting resin, an anaerobic resin, and an ultraviolet curable resin.

3. A method for producing a light guide unit comprising a bunch of glass fibers capable of transmitting light from a light source to a desired site, a sheath of a thermocontracting resin contracted to cover said bunch of glass fibers for substantially its overall length, and a filler of a hardening resin hardened to fill spaces between said glass fibers within said sheath, said method comprising:
   placing a bunch of glass fibers capable of transmitting light in a sheath of a thermocontracting resin,
   filling an interior of said sheath with a filler of a hardening resin so that spaces between said glass fibers are filled with said filler, thereby preparing a sheathed product,
   molding said sheathed product into a desired shape by placing the sheathed product in a mold having a cavity corresponding to said desired shape and applying heat and pressure, and
   hardening said filler in the sheathed product to fix a configuration of said sheathed product, whereby obtaining a light guide unit.

4. The method of claim 3 wherein said hardening resin is selected from the group consisting of a thermosetting resin, an anaerobic resin, and an ultraviolet curable resin.

5. The method of claim 4 wherein said filler of a thermosetting resin is hardened by heating.

6. The method of claim 5 wherein said hardening is effected during said molding by applying heat and pressure.

7. The method of claim 4 wherein said filler of an anaerobic resin is hardened by leaving a molded sheathed product to stand.

8. The method of claim 4 wherein said filler of an ultraviolet curable resin is hardened by irradiation with ultraviolet rays.

9. A dental handpiece comprising:
   a light guide unit for transmitting light from a light source to a treatment site,
   a channel for accommodating said light guide unit therein, and
   a light projection window in alignment with one end of said light guide unit for projecting light transmitted through the light guide unit onto a treatment site,
   wherein said light guide unit further comprises,
      a bunch of glass fibers capable of transmitting light from a light source to a treatment site,
      a sheath of a thermocontracting resin contracted to cover said bunch of glass fibers for substantially its overall length, and
      a filler of a hardening resin hardened to fill spaces between said fiber optics within said sheath.

* * * * *